United States Patent
Noh et al.

(10) Patent No.: US 8,947,756 B2
(45) Date of Patent: Feb. 3, 2015

(54) ELECTROCHROMIC MATERIAL AND ELECTROCHROMIC DEVICE INCLUDING THE SAME

(75) Inventors: Chang-Ho Noh, Suwon-si (KR);
Seog-Jin Jeon, Yongin-si (KR);
Seung-Uk Son, Suwon-si (KR)

(73) Assignee: Samsung Electronics Co., Ltd. (KR)

( * ) Notice: Subject to any disclaimer, the term of this patent is extended or adjusted under 35 U.S.C. 154(b) by 874 days.

(21) Appl. No.: 12/840,819

(22) Filed: Jul. 21, 2010

(65) Prior Publication Data

US 2011/0235151 A1 Sep. 29, 2011

(30) Foreign Application Priority Data

Mar. 23, 2010 (KR) .................. 10-2010-0025774

(51) Int. Cl.
| | |
|---|---|
| G02F 1/15 | (2006.01) |
| G02F 1/153 | (2006.01) |
| C07D 213/53 | (2006.01) |
| C07F 1/00 | (2006.01) |
| C07F 3/00 | (2006.01) |
| C07F 5/00 | (2006.01) |
| C07F 11/00 | (2006.01) |

(52) U.S. Cl.
CPC ............... *C07D 213/53* (2013.01); *C07F 1/005* (2013.01); *C07F 3/003* (2013.01); *C07F 5/003* (2013.01); *C07F 11/005* (2013.01); *G02F 1/1523* (2013.01); *G02F 1/1508* (2013.01)
USPC ........................... 359/265; 359/275; 359/273

(58) Field of Classification Search
USPC ......... 359/237, 242, 263–265, 275, 290–292, 359/295, 298, 245, 247, 272, 273; 252/583, 252/589, 584
See application file for complete search history.

(56) References Cited

U.S. PATENT DOCUMENTS

| | | | |
|---|---|---|---|
| 4,181,406 A * | 1/1980 | Kohara et al. ................. | 359/269 |
| 4,645,307 A * | 2/1987 | Miyamoto et al. ............ | 359/270 |
| 7,460,289 B2 * | 12/2008 | Pichot et al. .................. | 359/265 |
| 8,501,150 B2 * | 8/2013 | Schubert et al. .............. | 423/625 |
| 2003/0072071 A1 * | 4/2003 | Asano et al. .................. | 359/265 |
| 2006/0215250 A1 * | 9/2006 | Shibuya et al. ............... | 359/270 |
| 2008/0193734 A1 | 8/2008 | Whitnall et al. | |
| 2010/0090169 A1 * | 4/2010 | Cliff et al. .................... | 252/500 |
| 2010/0091352 A1 * | 4/2010 | Kokeguchi et al. ........... | 359/268 |

FOREIGN PATENT DOCUMENTS

| | | | |
|---|---|---|---|
| JP | 57-192483 A | 11/1982 | |
| JP | 08-110533 A | 4/1996 | |
| JP | 2007-112957 A | 5/2007 | |
| JP | 2008-248249 A | 10/2008 | |
| KR | 1020020062286 A | 7/2002 | |

(Continued)

OTHER PUBLICATIONS

Kolb, U. et al., The solid-state architecture of a metallosupramolecular polyelectrolyte, Proc Nati Acad Sci U S A. Jul. 5, 2006; 103(27): 10202-10206. Published online Jun. 26, 2006. doi: 10.1073/pnas.0601092103.

(Continued)

*Primary Examiner* — Joseph P Martinez
*Assistant Examiner* — Brandi Thomas
(74) *Attorney, Agent, or Firm* — Cantor Colburn LLP (57) ABSTRACT

An electrochromic material including a metal-organic framework including a metal, and an organic compound including a functional group, wherein the organic compound forms a coordination complex with the metal.

20 Claims, 4 Drawing Sheets

(56) References Cited

FOREIGN PATENT DOCUMENTS

| KR | 1020050037605 A | 4/2005 |
| WO | 97/35227 A2 | 9/1997 |

OTHER PUBLICATIONS

Ma B.-Q. et al., Microporous Pillared Paddle-Wheel Frameworks Based on Mixed-Ligand Coordination of Zinc Ions, Inorg. Chem., 2005, 44 (14), pp. 4912-4914.

Sun, Y.-Q. et al., Two-Dimensional Noninterpenetrating Transition Metal Coordination Polymers with Large Honeycomb-like Hexagonal Cavities Constructed from a Carboxybenzyl Viologen Ligand, Crystal Growth & Design, 2005,5 (5), pp. 1939-1943.

Garcia, H. et al., Semiconductor behavior of a metal-organic framework (MOF), Chemistry. 2007;13(18): pp. 5106-5112.

Kurth, D.G. et al., Transition metal ions: weak links for strong polymers, Soft Matter, 2006, 2, pp. 915-927, DOI: 10.1039/b607485e.

\* cited by examiner

ELECTROCHROMIC MATERIAL AND ELECTROCHROMIC DEVICE INCLUDING THE SAME

CROSS-REFERENCE TO RELATED APPLICATION

This application claims priority to Korean Patent Application No. 10-2010-0025774, filed on Mar. 23, 2010, and all the benefits accruing therefrom under 35 U.S.C. §119, the content of which in its entirety is herein incorporated by reference.

BACKGROUND

1. Field

This disclosure relates to an electrochromic material and an electrochromic device including the same.

2. Description of the Related Art

Electrochromism refers to a phenomenon in which a color of a material may be reversibly changed according to a direction of an electric field when a voltage is applied. A material having such property, that is, a material whose optical characteristics may be reversibly changed by an electrochemical redox reaction, is called an electrochromic material. An electrochromic material be colorless until an electric field is applied thereto, or conversely it may be colored in the absence of an applied electric field and lose the color and become colorless when an electric field is applied.

Electrochromic materials have been applied in electrochromic devices wherein light transmission characteristics change according to an applied voltage. For example, smart windows are an example of an electrochromic device which utilizes electrochromic light transmission characteristics. Recently electrochromic materials have also been utilized in display devices, such as electronic paper, due to the excellent portability and light weight of such devices.

In a commercially available electrochromic device, an electrochromic material is fixed on an electrode. The electrochromic material is fixed by providing an additional conductive material, such as titanium oxide ($TiO_2$), on the electrode and adsorbing the electrochromic material using the same. However, such a fixing process includes a heat treatment at a high temperature, and the electrochromic material is easily removed, and thus may undesirably deteriorate, degrading the reliability of a device.

Accordingly, there remains a need for an improved electrochromic material and an improved method to manufacture an electrochromic device.

SUMMARY

An aspect provides an electrochromic material capable of simplifying a process of manufacturing an electrochromic device and improving the reliability of such a device.

Another aspect provides an electrochromic device including the electrochromic material.

According to an aspect, an electrochromic material is provided which includes a metal-organic framework including a metal, and an organic compound including a functional group, wherein the organic compound forms a coordination complex with the metal.

According to another aspect, an electrochromic device is provided which includes a first electrode and a second electrode opposite the first electrode, an electrochromic layer disposed on the first electrode or the second electrode, the electrochromic layer including an electrochromic material; and an electrolyte disposed between the first electrode and the second electrode, wherein the electrochromic material includes a metal-organic framework including a metal and an organic compound including a functional group, wherein the organic compound forms a coordination complex with the metal.

The metal may include a light metal, a transition element, a lanthanide metal, an alkali metal, or a combination thereof.

The metal may include beryllium (Be), barium (Ba), copper (Cu), zinc (Zn), cerium (Ce), magnesium (Mg), aluminum (Al), titanium (Ti), or a combination thereof.

The functional group may include a carboxyl group, a pyridyl group, an imidazolyl group, or a combination thereof.

The organic compound may include a substituted or unsubstituted viologen, a substituted or unsubstituted anthraquinone, or a combination thereof.

The metal-organic framework may be soluble in a solvent.

The metal-organic framework may be a porous material.

The metal-organic framework may include a complex represented by the following Chemical Formula 1 or Chemical Formula 2.

[Chemical Formula 1]

[Chemical Formula 2]

In the above Chemical Formula 1 or Chemical Formula 2, M is a metal, ECM is an organic compound which can be oxidized and reduced, $L_1$ and $L_2$ are each independently a single bond, a substituted or unsubstituted C1 to C30 alkylene group, a substituted or unsubstituted C3 to C30 cycloalkylene group, a halogen-containing group, or a combination thereof, $X_1$ and $X_2$ are each independently a functional group which forms a coordination complex with the metal, and n is 1 to about 5.

The M may be beryllium (Be), barium (Ba), copper (Cu), zinc (Zn), cerium (Ce), magnesium (Mg), aluminum (Al), titanium (Ti), or a combination thereof; the ECM may be a substituted or unsubstituted viologen, a substituted or unsubstituted anthraquinone, or a combination thereof; and the $X_1$ and $X_2$ are each a carboxyl group.

The electrochromic material may be a film on the first electrode or the second electrode.

The electrochromic material may be directly on the first electrode or the second electrode.

The first electrode or the second electrode may include a transparent conductor, and the transparent conductor may include indium tin oxide (ITO), fluorine tin oxide (FTO), antimony doped tin oxide (ATO), an organic conductive material, or a combination thereof.

BRIEF DESCRIPTION OF THE DRAWINGS

The above and other aspects, advantages and features of this disclosure will become more apparent by describing in further detail exemplary embodiments thereof with reference to the accompanying drawings, in which.

DETAILED DESCRIPTION

Exemplary embodiments will be described more fully hereinafter with reference to the accompanying drawings. This disclosure may, however, be embodied in many different forms, and should not be construed as limited to the exemplary embodiments set forth herein.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present invention.

The terminology used herein is for the purpose of describing particular embodiments only and is not intended to be limiting. As used herein, the singular forms "a," "an," and "the" are open terms that may be used in conjunction with the plural forms as well, unless the context clearly indicates otherwise.

It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another elements as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

As used herein, when a definition is not otherwise provided, the term "substituted" refers to a compound substituted with at least one (e.g., 1, 2, 3, 4, 5, 6 or more) substituents selected from a halogen (F, C, Br, I), a hydroxyl group, an alkoxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid group or a salt thereof, a C1 to C20 alkyl group, a C2 to C16 alkynyl group, a C6 to C20 aryl group, a C7 to C13 arylalkyl group, a C1 to C4 oxyalkyl group, a C1 to C20 heteroalkyl group, a C3 to C20 heteroarylalkyl group, a C3 to C20 cycloalkyl group, a C3 to C15 cycloalkenyl group, a C6 to C15 cycloalkynyl group, a C2 to C20 heterocycloalkyl group, or a combination thereof, instead of hydrogen, provided that the substituted atom's normal valence is not exceeded.

Hereinafter, the electrochromic material according to an embodiment is further disclosed.

An electrochromic material according to an embodiment includes a metal-organic framework comprising a metal and an organic compound comprising a functional group, wherein the organic compound forms a coordination complex with the metal.

The metal may include a light metal, a transition element, a lanthanide metal, an alkali metal, or a combination thereof. The metal may include, for example, beryllium (Be), barium (Ba), copper (Cu), zinc (Zn), cerium (Ce), magnesium (Mg), aluminum (Al), titanium (Ti), or a combination thereof.

The organic compound includes a color changing part and a functional group. While not wanting to be bound by theory, the color changing part may express a color depending upon an oxidation state of the color changing part, wherein the oxidation state may be selected using a redox reaction by applying an electric field. In an embodiment, the organic compound may form a coordination complex with the metal through the functional group.

The organic compound may have a structure represented by, for example, the following Chemical Formula A.

[Chemical Formula A]

In Chemical Formula A, ECM is a color changing part which may be oxidized and reduced, $X_1$ and $X_2$ are each independently a functional group which may coordinate with a metal, and $L_1$ and $L_2$ are connectors, each of which may respectively connect the color changing part to the functional group.

ECM may be, for example, a substituted or unsubstituted viologen (e.g., a viologen derivative), a substituted or unsubstituted anthraquinone (e.g., an anthraquinone derivative), or a combination thereof. In an embodiment, the viologen is a derivative of 4,4'-bipyridyl and is a part that reversibly changes color by a redox reaction when oxidized or reduced. In other words, it may be substantially colorless (e.g., not express color) when the viologen is oxidized, and it may express color when it is reduced.

$X_1$ and $X_2$ are each independently, for example, a carboxyl group, a pyridyl group, an imidazolyl group, or a combination thereof. Also, n may be 1 to about 5, specifically about 2 to about 4, more specifically 3.

$L_1$ and $L_2$ are each independently a single bond, a substituted or unsubstituted C1 to C30 alkylene group, a substituted or unsubstituted C3 to C30 cycloalkylene group, a halogen-containing group, or a combination thereof.

The organic compound may be, for example, a compound represented by the following Chemical Formulas A-1 to A-5.

(A-1)

(A-2)

(A-3)

(A-4)

(A-5)

The metal-organic framework may be obtained by contacting a metal precursor with an organic compound in a solvent.

The metal precursor may be a salt, for example, an acetate, a carbonyl, a carbonate, a nitrate, a sulfate, a phosphate, a halide, or the like, or a combination comprising at least one of the foregoing.

The solvent is not limited as long as it may dissolve the metal precursor and the organic compound, and examples thereof may include at least one of deionized water, methanol, ethanol, propanol, isopropanol, 2-methoxyethanol, 2-ethoxyethanol, 2-propoxyethanol 2-butoxyethanol, methylcellosolve, ethylcellosolve, diethyleneglycol methylether, diethyleneglycol ethylether, dipropyleneglycol methylether, toluene, xylene, hexane, heptane, octane, ethyl acetate, butyl acetate, diethyleneglycol dimethylether, diethyleneglycol dimethylethylether, methyl methoxy propionate, ethylethoxy propionate, ethyl lactate, propyleneglycol methylether acetate, propyleneglycol methylether, propyleneglycol propylether, methylcellosolve acetate, ethylcellosolve acetate, diethyleneglycol methylacetate, diethyleneglycol ethylacetate, acetone, methylisobutylketone, cyclohexanone, dimethyl formamide ("DMF"), N,N-dimethyl acetamide ("DMAc"), N-methyl-2-pyrrolidone, γ-butyrolactone, diethylether, ethyleneglycol dimethylether, diglyme, tetrahydrofuran, acetylacetone, or acetonitrile.

The metal-organic framework may include, for example, a complex represented by the following Chemical Formula 1 or 2.

[Chemical Formula 1]

[Chemical Formula 2]

In Chemical Formula 1 or Chemical Formula 2, ECM, $L_1$, $L_2$, $X_1$, $X_2$, and n may be as defined above, respectively.

In an embodiment, M is a metal, and may be, for example, beryllium (Be), barium (Ba), copper (Cu), zinc (Zn), cerium (Ce), magnesium (Mg), aluminum (Al), to titanium (Ti), or a combination thereof.

In Chemical Formula 1 or Chemical Formula 2, ECM is an organic compound which may be oxidized and reduced, and may be, for example, a substituted or unsubstituted viologen, a substituted or unsubstituted anthraquinone, or a combination thereof.

In Chemical Formula 1 or Chemical Formula 2, $L_1$ and $L_2$ are linkers, and are each independently a single bond, a substituted or unsubstituted C1 to C30 alkylene group, a substituted or unsubstituted C3 to C30 cycloalkylene group, a halogen-containing group, or a combination thereof.

$X_1$ and $X_2$ are each a functional group which may form a coordination complex with a metal, and may each independently be a carboxyl group.

In an embodiment, n is 1 to about 5, specifically 1 to about 3, more specifically 2.

The metal-organic framework may be have various structures, and is not limited to the complex represented by Chemical Formula 1.

The metal-organic framework may have a porous structure.

Figure 1:
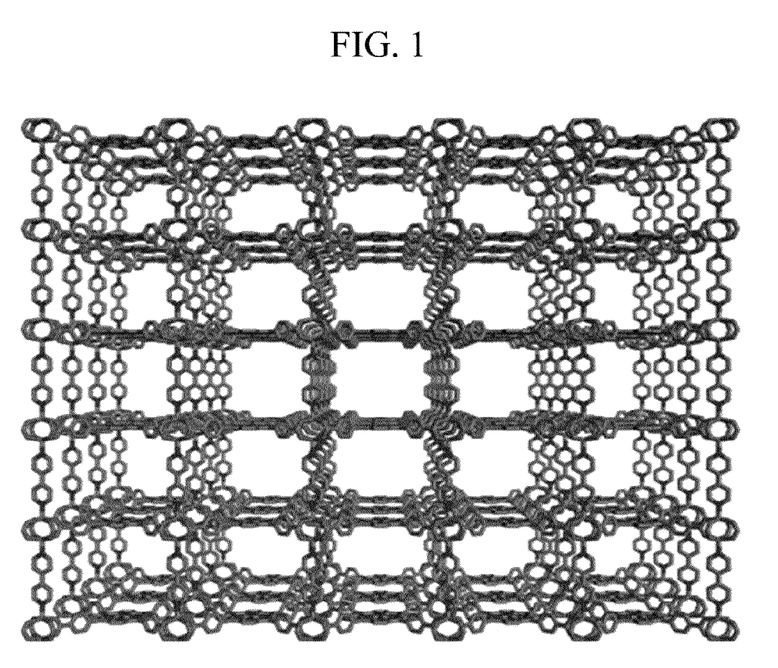
FIG. 1 is a schematic view of an exemplary embodiment of a metal-organic framework, showing a porous structure of a metal-organic framework represented by Chemical Formula 1.

FIG. 1 is a schematic view showing the porous structure of an exemplary embodiment of the metal-organic framework represented by Chemical Formula 1.

Referring to FIG. 1, it is confirmed that in an embodiment, the metal-organic framework represented by Chemical Formula 1 has a porous structure in which the metal-organic framework is repeatedly bound in a row direction and in a column direction.

Through the porous structure of the metal-organic framework, ions may be transported, and the metal-organic framework may be oxidized and reduced by the ion transport to exhibit the electrochromic characteristics.

In addition, the stability of the metal-organic framework to reduction and oxidation is further improved by the metal included in metal-organic framework, enhancing the reliability of the electrochromic material compared to a comparative electrochromic material including only an organic compound.

The particle size of the metal-organic framework may be controlled by the synthesis conditions. For example, a millimeter-sized crystal or a micrometer-sized crystal of the metal-organic framework may be prepared by selecting synthesis temperature, synthesis time, the type of solvent, or the like.

The metal-organic framework may be soluble. In an embodiment, the metal-organic framework may be dissolved in a solvent to form a solution, and the solution coated on an electrode to provide a film. Inclusion of an additional conductive material for fixing the electrochromic material on an electrode may be omitted if desired.

Generally, in order to fix an electrochromic material on an electrode, an additional conductive material such as titanium oxide ($TiO_2$) is provided on the electrode and the additional conductive material is adsorbed with the electrochromic material. In a comparative process, the fixing of an electrochromic material to an electrode includes a heating process, and a temperature of the heating process may be about 450° C. or higher in order to provide the conductive material, which may be titanium oxide ($TiO_2$).

According to an embodiment, because the conductive material may be omitted, a process for fixing an electrochromic material to an electrode may be simplified. In addition, because the heating process, which may include heating at a high temperature, may be omitted, the disclosed process may be used with flexible (e.g., polymeric) materials, thus flexible materials may be used in the fabrication of a flexible device. In addition, the electrochromic material is not released (e.g., the electrochromic material is adhered to the substrate), thereby enhancing the reliability of the device.

The electrochromic device including the electrochromic material is further described with reference to FIG. 2.

Figure 2:
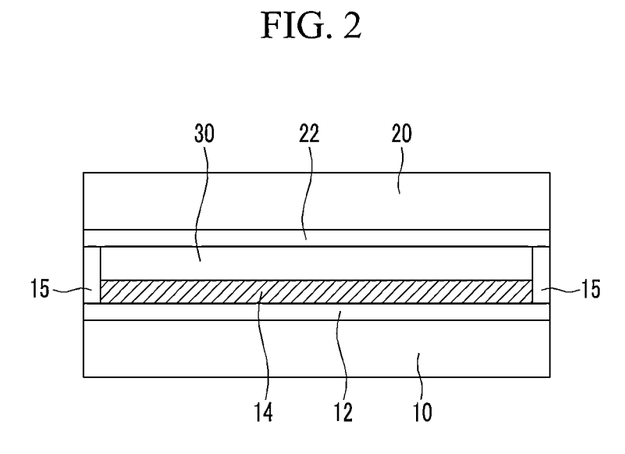
FIG. 2 is a schematic cross-sectional view showing of an exemplary embodiment of an electrochromic device.

FIG. 2 is a schematic cross-sectional view of an exemplary embodiment of an electrochromic device.

Referring to FIG. 2, the electrochromic device according to an embodiment includes a pair of insulation substrates, a first insulation substrate 10 and a second insulation substrate 20, facing each other (i.e., opposite each other), and a first electrode 12 and a second electrode 22 positioned on the first and second insulation substrates 10 and 20, respectively.

The first and second insulation substrates 10 and 20 may comprise transparent glass, plastic, or a combination comprising at least one of the foregoing. Examples of the plastic include one or more selected from polyacrylate, polyethylene etherphthalate, polyethylene naphthalate, polycarbonate, polyarylate, polyetherimide, polyethersulfone, or polyimide.

The first electrode 12 includes a transparent conductor, and the transparent conductor may be, for example, and inorganic conductive material including indium tin oxide ("ITO"), fluorine tin oxide ("FTO"), antimony doped tin oxide ("ATO"), an organic conductive materials such as polyacetylene or polythiophene, or a combination comprising at least one of the foregoing.

The second electrode 22 may comprise a transparent or opaque conductive material, and may be, for example, indium tin oxide ("ITO"), fluorine tin oxide ("FTO"), a metal such as Al, antimony-doped tin oxide ("ATO"), or a combination thereof.

In an embodiment, on the first electrode 12, an electrochromic layer 14 including the electrochromic material is provided. The electrochromic layer 14 may be formed on the first electrode 12, may have a film shape, and may be directly on the first electrode 12 without a buffer layer for adsorption of the electrochromic material.

The first substrate 10 and the second substrate 20 may be fixed by a spacer 15, and an electrolyte 30 may be disposed (e.g., filled) between the first substrate 10 and the second substrate 20. The electrolyte 30 may provide an oxidation/reduction material contacting (e.g., for reacting with) the electrochromic material, and the electrolyte may be a liquid electrolyte or a solid polymer electrolyte. The liquid electrolyte may, for example, include a solution wherein a lithium salt such as LiOH or $LiClO_4$, a potassium salt such as KOH, or a sodium salt such as NaOH, is dissolved in a solvent, or a combination comprising at least one of the foregoing, but is not limited thereto. The solid electrolyte may include poly(2-acrylamino-2-methylpropane sulfonic acid), or polyethylene oxide, or a combination comprising at least one of the foregoing, but is not limited thereto.

The following examples further illustrate this disclosure in additional detail. Also, it is to be understood that this disclosure is not limited by these examples.

Example 1

Synthesis of the Organic Compound

A 1.5 g (10 millimole, mmol) quantity of 4,4-bipyridyl and 5 equivalents of 2,4-dichloro-nitrobenzene are introduced into 20 ml of acetonitrile and reacted at 80° C. for 72 hours. Then the obtained compound is cooled to room temperature to provide a white compound represented by Chemical Formula a-1. The yield is about 60%.

Chemical Formula a-1

(a-1)

Subsequently, the white compound (i.e., the a-1 compound) and 3 equivalents of 4-aminophenylacetic acid are introduced into a mixed solvent including ethanol and water at an 8:2 volume ratio and reacted at 100° C. for 12 hours and then cooled to room temperature. The obtained compound is extracted with chloroform and water, and an aqueous solution layer is gathered to provide the compound according to Chemical Formula A-1 (i.e., the A-1 compound) by removing the solvent. The yield is about 80%.

Chemical Formula A-1

(A-1)

Synthesis of the Metal-Organic Framework ("MOF")

A 0.30 g (0.60 mmol) quantity of an organic compound represented by Chemical Formula A-1 and 1.1 equivalents of barium carbonate ($BaCO_3$) are mixed in 10 ml of deionized water. The resulting mixture is agitated at room temperature for 48 hours, and water is removed under vacuum to provide a barium-viologen complex represented by the following Chemical Formula B-1.

Chemical Formula B-1

(B-1)

Fabrication of an Electrochromic Device

The barium-viologen complex represented by Chemical Formula B-1 is dissolved in a mixed solvent, including methanol and butanol at a 4:1 volume ratio, to provide each of a 0.53 weight percent ("wt %"), 1.24 wt %, 1.36 wt %, 1.49 wt %, and a 1.70 wt % precursor solution.

An ITO electrode is formed on a polymer substrate and spin-coated with the precursor solution thereon five times and dried at 80° C. An ITO electrode is formed on another polymer substrate, and then the two electrodes are disposed to face each other and sealed with spacers and injected with electrolyte in which 0.05 mmol of $LiClO_4$ is dissolved in butyroacetone to provide an electrochromic device.

Example 2

Synthesis of Organic Compound

A 1.5 g (10 mmol) quantity of 4,4-bipyridyl and 5 equivalents of 2,4-dichloronitrobenzene are introduced into 20 ml of acetonitrile and reacted at 80° C. for 72 hours. The obtained compound is cooled to room temperature to provide a white compound of Chemical Formula, i.e., the a-1 compound. The yield is about 60%.

Subsequently, the a-1 compound and 3 equivalents of 4-aminobenzoic acid are introduced into a mixed solvent (4-aminobenzoic acid) including ethanol and water at an 8:2 volume ratio and reacted at 100° C. for 12 hours and cooled to room temperature. After extracting the obtained compound with chloroform and water, aqueous solution layers are gathered, and a solvent is removed to provide an organic compound represented by the following Chemical Formula A-2. The yield is about 85%.

Chemical Formula A-2

(A-2)

Synthesis of a Metal-Organic Framework ("MOF")

A 0.47 g (1 mmol) quantity of the organic compound represented by Chemical Formula A-2 and 2.2 equivalents of cerium nitrate ($Ce(NO_3)_3$) are mixed in 10 ml of a mixed solvent including deionized water and dimethylformaldehyde ("DMF") in a 1:3 volume ratio, and three drops of hydrochloric acid (HCl) (35.0-37.0 vol %, Samiun Chemicals) is added thereto. After being allowed to stand at 80° C. for 3 days, a crystal is separated by filtration and the crystal dried under reduced pressure for 12 hours to provide a colorless cerium-viologen complex represented by Chemical Formula B-2.

Chemical Formula B-2

(B-2)

Fabrication of Electrochromic Device

A cerium-viologen complex represented by Chemical Formula B-2 is dissolved in butanol to provide a 3 wt % precursor solution.

An ITO electrode is formed on a polymer substrate and coated with the precursor solution thereon by spin coating at 1000 revolutions per minute ("rpm") for 5 seconds, at 2000 rpm for 10 seconds, and at 1000 rpm for 5 seconds and dried at 80° C. for one hour. An ITO electrode is formed on another polymer substrate, and then the two electrodes are disposed to face each other, are sealed with spacers, and injected with an electrolyte, in which 0.05 mmol of $LiClO_4$ is dissolved in butyroacetone, to provide an electrochromic device.

Example 3

Synthesis of an Organic Compound

A 1.5 g (10 mmol) quantity of 4,4-bipyridyl and 5 equivalents of 2,4-dichloronitrobenzene are introduced into 20 ml of acetonitrile and reacted at 80° C. for 72 hours. The obtained compound is cooled to room temperature to provide a white compound according to Chemical Formula a-1 (i.e., the a-1 compound). The yield is about 60%.

Then the a-1 compound and 5 equivalents of 5-aminoisophthalic acid are introduced into a mixed solvent including ethanol and water at an 8:2 volume ratio and reacted at 100° C. for 12 hours and then cooled to room temperature. After extracting the obtained compound with chloroform and water, an aqueous solution layer is gathered and the solvent removed to provide an organic compound represented by the following Chemical Formula A-3. The yield is about 98%.

Chemical Formula A-3

(A-3)

Synthesis of a Metal-Organic Framework ("MOF")

A 0.56 g (1 mmol) quantity of the organic compound represented by Chemical Formula A-3 and 4.4 equivalents of cerium nitrate $(Ce(NO_3)_3)$ are mixed in 10 ml of a mixed solvent including deionized water and dimethylformaldehyde ("DMF") at a 1:3 volume ratio, and three drops of hydrochloric acid (HCl) is added thereto. After being allowed to stand at 80° C. for 3 days, a crystal is separated by filtration and dried under a reduced pressure for 12 hours to provide a colorless cerium-viologen complex.

Fabrication of an Electrochromic Device

An electrochromic device is fabricated using the same procedure as in Example 2, except that a cerium-viologen complex is used as a metal-organic framework ("MOF").

Example 4

Synthesis of an Organic Compound

A 3 g (20 mmol) quantity of 4,4-bipyridyl and 3 equivalents of bromo-p-toluic acid are introduced into 20 ml of acetonitrile and reacted at 100° C. for 24 hours. The obtained compound is cooled to room temperature to provide a yellow crystalline compound of Chemical Formula A-4, i.e., the A-4 compound. The yield is about 85%.

(A-4)

Synthesis of a Metal-Organic Framework ("MOF")

A 0.5 g (1 mmol) quantity of the organic compound represented by Chemical Formula A-4 and 2.2 equivalents of copper nitrate $(Cu(NO_3)_2)$ are mixed in 10 ml of DMF. The mixture is allowed to stand at about 110° C. for 3 days to provide a blue solid. Then the blue solid is dried under vacuum to remove the solvent, so as to provide a blue copper-viologen complex.

Fabrication of Electrochromic Device

An electrochromic device is fabricated in the same procedure as in Example 2, except that a copper-viologen complex is used as a metal-organic framework ("MOF").

Example 5

Synthesis of Organic Compound

A 2.86 g (42 mmol) quantity of isoprene and 1.1 equivalents of p-benzoquinone are dissolved in 20 ml of acetic acid. Next, 2.5 equivalents of chromium (VI) oxide are introduced thereto and reacted at 70° C. for 48 hours. Subsequently, the solvent is removed to provide a product. To separate a white compound of Chemical Formula a-5, i.e., the a-5 compound, from the product, a silica column and a mixed solvent including hexane and ether at a 5:1 volume ratio were used. The yield is about 45%.

Chemical Formula a-5

(a-5)

Then the a-5 compound and 1.1 equivalents of isoprene are introduced into acetic acid and reacted at room temperature for 24 hours to remove the solvent. The resulting material is then dissolved in 40 ml of ethanol and 15 ml of a 5% potassium hydroxide aqueous solution and reacted at room temperature for 4 hours. After the reaction, the pH is adjusted to 5 with hydrochloric acid to provide a white compound represented by the following Chemical Formula a-5', i.e., the a-5' compound.

Chemical Formula a-5'

(a-5')

The a-5' compound and chromium oxide are dissolved in acetic acid and reacted for 24 hours, and then a solvent is removed. A 30 ml quantity of acetone is introduced thereto and agitated for 20 minutes to provide a white powder. Then the white powder is filtered and dried under vacuum to provide a compound represented by the following Chemical Formula A-5. The yield is about 40%.

Chemical Formula A-5

(A-5)

Synthesis of Metal-Organic Framework (MOF)

A 0.3 g (1 mmol) quantity of the organic compound represented by the above Chemical Formula A-5 and 2.2 equivalents of copper nitrate ($Cu(NO_3)_2$) are mixed in 10 ml of DMF. After being allowed to stand at about 110° C. for 24 hours, the solvent is removed under vacuum to provide a copper-organic material complex represented by the following Chemical Formula B-5.

Chemical Formula B-5

(B-5)

Fabrication of Electrochromic Device

An electrochromic device is fabricated using the same procedure as in Example 2, except that a copper-organic complex is used as a metal-organic composite framework ("MOF").

Assessment—1

The electrochromism is monitored while applying a voltage of 0 V to 1.8 V to the electrochromic device according to Example 1.

FIG. 3(a) is a photograph showing the color change before applying a voltage to the electrochromic device according to Example 1, FIG. 3(b) is a photograph showing the color change after applying a voltage in a 1-electron reduction, and FIG. 3(c) is a photograph showing the color change in a 2-electron reduction.

Figure 3:
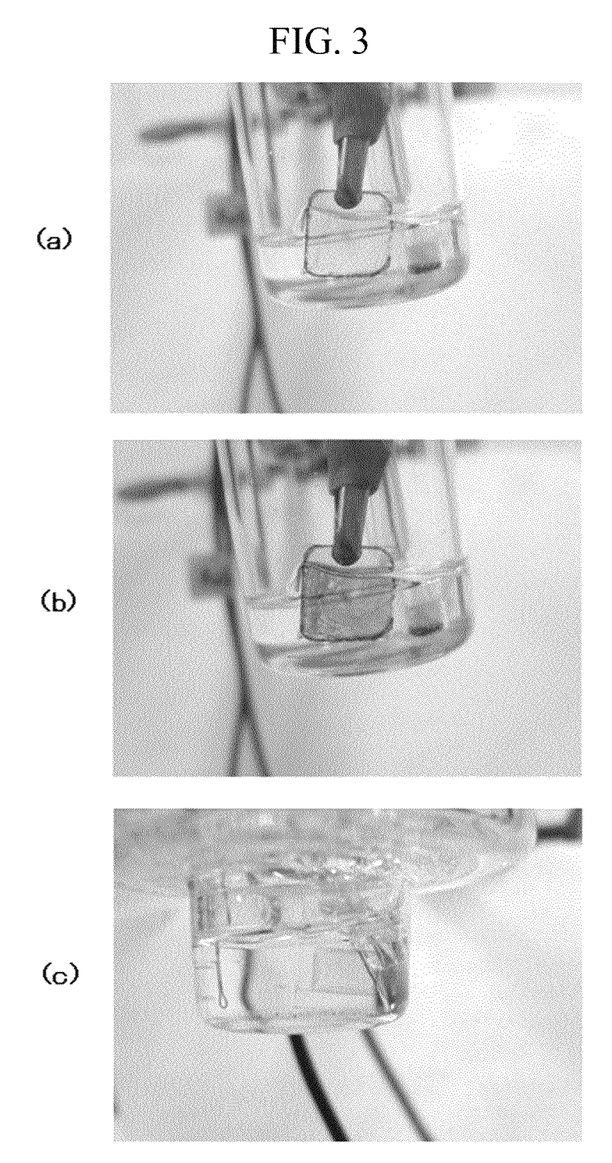
FIG. 3(a) is a photograph showing the color change before applying a voltage to an electrochromic device according to Example 1.
FIG. 3(b) and FIG. 3(c) are photographs showing the color change after applying a voltage to an electrochromic device according to Example 1.

Referring to FIG. 3, it is confirmed that the electrochromic device according to Example 1 does not express color before applying a voltage to an electrochromic device according to Example 1, and expresses green after applying a voltage, as shown in FIGS. 3(b) and 3(c).

Assessment—2

A voltage of 0 V to 2.2 V is applied to the electrochromic device obtained from Example 5 to observe the electrochromism.

Figure 4:
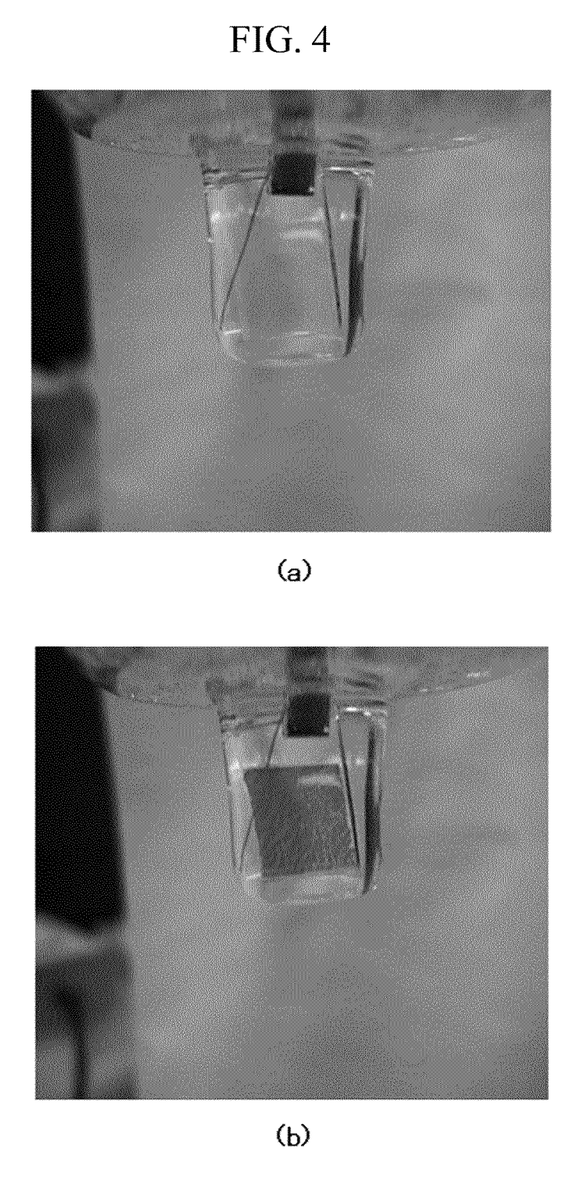
FIG. 4(a) is a photograph showing the color change before applying a voltage to an electrochromic device according to Example 5.
FIG. 4(b) is photograph showing the color change after applying a voltage.

FIG. 4(a) is a photograph showing color change before applying a voltage to the electrochromic device obtained from Example 5, and FIG. 4(b) is a photograph showing color change after applying a voltage to the electrochromic device obtained from Example 5.

Referring to FIG. 4(a), it is confirmed that the electrochromic device obtained from Example 5 does not express color before applying voltage, and expresses a blue color after applying a voltage, as shown in FIG. 4(b).

From the results, the electrochromic characteristics are shown according to the examples.

While this disclosure has been described in connection with what practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. An electrochromic material comprising:
   a metal-organic framework comprising
      a metal, and
      an organic compound comprising a color changing part and a functional group,
   wherein the organic compound forms a coordination complex with the metal, and
   wherein the organic compound comprises a substituted or unsubstituted viologen, a substituted or unsubstituted anthraquinone, or a combination thereof.

2. The electrochromic material of claim 1, wherein the metal comprises a light metal, a transition element, a lanthanide metal, an alkali metal, or a combination thereof.

3. The electrochromic material of claim 1, wherein the metal comprises beryllium, barium, copper, zinc, cerium, magnesium, aluminum, titanium, or a combination thereof.

4. The electrochromic material of claim 1, wherein the functional group comprises a carboxyl group, a pyridyl group, an imidazolyl group, or a combination thereof.

5. The electrochromic material of claim 1, wherein the metal-organic framework is soluble in a solvent.

6. The electrochromic material of claim 1, wherein the metal-organic framework is a porous material.

7. An electrochromic material comprising:
   a metal-organic framework comprising
      a metal, and
      an organic compound comprising a color changing part and a functional group,
   wherein the organic compound forms a coordination complex with the metal, and
   wherein the metal-organic framework comprises a complex represented by the following Chemical Formula 1 or Chemical Formula 2:

[Chemical Formula 1]

[Chemical Formula 2]

wherein, in the above Chemical Formula 1 or Chemical Formula 2, M is a metal, ECM is an organic group which can be oxidized and reduced, $L_1$ and $L_2$ are each independently a single bond, a substituted or unsubstituted C1 to C30 alkylene group, a substituted or unsubstituted C3 to C30 cycloalkylene group, a halogen-containing group, or a combination thereof, $X_1$ and $X_2$ are each independently a functional group which forms a coordination complex with the metal, and n is 1 to about 5.

8. The electrochromic material of claim 7, wherein
M is beryllium, barium, copper, zinc, cerium, magnesium, aluminum, titanium, or a combination thereof;
ECM is a substituted or unsubstituted viologen, a substituted or unsubstituted anthraquinone, or a combination thereof; and
$X_1$ and $X_2$ are each a carboxyl group.

9. An electrochromic device comprising:
a first electrode and a second electrode opposite the first electrode;
an electrochromic layer disposed on the first electrode or the second electrode, the electrochromic layer comprising an electrochromic material; and
an electrolyte disposed between the first electrode and the second electrode,
wherein the electrochromic material comprises a metal-organic framework comprising a metal and an organic compound comprising a color changing part and a functional group, wherein the organic compound forms a coordination complex with the metal, and
wherein the organic compound comprises a substituted or unsubstituted viologen, a substituted or unsubstituted anthraquinone, or a combination thereof.

10. The electrochromic device of claim 9, wherein the metal comprises a light metal, transition element, a lanthanide metal, an alkali metal, or a combination thereof.

11. The electrochromic device of claim 9, wherein the metal comprises beryllium, barium, copper, zinc, cerium, magnesium, aluminum, titanium, or a combination thereof.

12. The electrochromic device of claim 9, wherein the functional group comprises a carboxyl group, a pyridyl group, an imidazolyl group, or a combination thereof.

13. The electrochromic device of claim 9, wherein the electrochromic layer is a film on the first electrode or the second electrode.

14. The electrochromic device of claim 13, wherein the electrochromic layer is directly on the first electrode or the second electrode.

15. The electrochromic device of claim 14, wherein the first electrode or the second electrode comprises a transparent conductor.

16. The electrochromic device of claim 15, wherein the transparent conductor comprises indium tin oxide, fluorine tin oxide, antimony doped tin oxide, an organic conductive material, or a combination thereof.

17. An electrochromic device comprising:
a first electrode and a second electrode opposite the first electrode;
an electrochromic layer disposed on the first electrode or the second electrode, the electrochromic layer comprising the electrochromic material of claim 7; and
an electrolyte disposed between the first electrode and the second electrode.

18. The electrochromic device of claim 17, wherein in Chemical Formula 1 and Chemical Formula 2
M is beryllium, barium, copper, zinc, cerium, magnesium, aluminum, titanium, or a combination thereof;
ECM is a substituted or unsubstituted viologen, a substituted or unsubstituted anthraquinone, or a combination thereof; and
$X_1$ and $X_2$ are each a carboxyl group.

19. The electrochromic material of claim 1, wherein the metal forms a coordination complex with at least two molecules of the organic compound.

20. The electrochromic material of claim 1, wherein the organic compound comprises a compound represented by Chemical Formulas (A-1) to (A-5):

(A-1)

(A-2)

(A-3)

(A-4)

(A-5)

* * * * *